United States Patent
De Haan et al.

(10) Patent No.: US 11,712,185 B2
(45) Date of Patent: Aug. 1, 2023

(54) DEVICE, SYSTEM AND METHOD FOR EXTRACTING PHYSIOLOGICAL INFORMATION INDICATIVE OF AT LEAST ONE VITAL SIGN OF A SUBJECT

(71) Applicant: KONINKLIJKE PHILIPS N.V., Eindhoven (NL)

(72) Inventors: Gerard De Haan, Helmond (NL); Calina Ciuhu-Pijlman, Eindhoven (NL); Caifeng Shan, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 382 days.

(21) Appl. No.: 17/041,512

(22) PCT Filed: Mar. 20, 2019

(86) PCT No.: PCT/EP2019/056914
§ 371 (c)(1),
(2) Date: Sep. 25, 2020

(87) PCT Pub. No.: WO2019/185410
PCT Pub. Date: Oct. 3, 2019

(65) Prior Publication Data
US 2021/0361203 A1    Nov. 25, 2021

(30) Foreign Application Priority Data
Mar. 27, 2018 (EP) ..................... 18164137

(51) Int. Cl.
*A61B 5/1455*    (2006.01)
*A61B 5/00*    (2006.01)
*A61B 5/024*    (2006.01)

(52) U.S. Cl.
CPC ........ *A61B 5/14558* (2013.01); *A61B 5/0075* (2013.01); *A61B 5/0077* (2013.01); *A61B 5/02416* (2013.01); *A61B 5/7221* (2013.01)

(58) Field of Classification Search
CPC ... A61B 5/145; A61B 5/1455; A61B 5/14558; A61B 5/0075; A61B 5/0077;
(Continued)

(56) References Cited

U.S. PATENT DOCUMENTS

2004/0246490 A1* 12/2004 Wang ................. G01B 9/02091
356/479
2012/0321759 A1   12/2012 Marinkovich
(Continued)

FOREIGN PATENT DOCUMENTS

WO    2017121834 A1    7/2017

OTHER PUBLICATIONS

International Search Report dated Jun. 4, 2019.
(Continued)

*Primary Examiner* — Devin B Henson
*Assistant Examiner* — Evelyn Grace Park

(57) ABSTRACT

The present disclosure relates to devices, systems and methods for extracting physiological information indicative of at least one vital sign of a subject. An embodiment of a device comprises a pre-treatment unit configured to derive at least three detection signals from electromagnetic radiation reflected from a skin region of a subject, wherein at least two detection signals comprise wavelength-dependent reflection information in a different wavelength channel and at least two detection signals comprise reflection information in different polarization channels having different polarization directions.

15 Claims, 3 Drawing Sheets

(58) Field of Classification Search
CPC ....... A61B 5/024; A61B 5/02416; A61B 5/72; A61B 5/7221; A61B 2562/0233
See application file for complete search history.

(56) References Cited

U.S. PATENT DOCUMENTS

| | | |
|---|---|---|
| 2013/0271591 A1 | 10/2013 | Van Leest |
| 2015/0366492 A1 | 12/2015 | De Haan |
| 2016/0120482 A1* | 5/2016 | Kirenko ............. A61B 5/02416 600/479 |
| 2017/0007138 A1 | 1/2017 | Kim |
| 2017/0086755 A1 | 3/2017 | De Haan |
| 2019/0000391 A1 | 1/2019 | De Haan |

OTHER PUBLICATIONS

G. De Haan & A. Van Leest, "Improved Motion Robustness of Remote-PPG by Using the Blood Volume Pulse Signature", Physiol. Meas. 35 1913, 2014.

M. Van Gastel, S. Stuijk and G. De Haan, "Motion Robust Remote-PPG in Infrared", IEEE, Tr. on Biomedical Engineering, vol. 62, No. 5, 2015, pp. 1425-1433.

A. A. Kamshilin, E. Nippolainen, I. S. Sidorov, P. V. Vasilev, N. P. Erofeev, N. P. Podolian, and R. V. Romashko, "A New Look at the Essence of the Imaging Photoplethysmography," Sci. Rep. 5, 10494 (2015).

Deepak Mishra, Neha Priyadarshini, Supriya Chakraborty and Mukul Sarkar, "Blood Oxygen Saturation Measurement Using Polarization-Dependent Optical Sectioning", IEEE Sensors Journal, vol. 17., No. 12, Jun. 15, 2017, pp. 3900-3908.

Van Gastel, M. et al., "New principle for measuring arterial blood oxygenation, enabling motion-robust remote monitoring", Scientific Reports, vol. 6, No. 1, (Dec. 7, 2016), pp. 1-16.

* cited by examiner

DEVICE, SYSTEM AND METHOD FOR EXTRACTING PHYSIOLOGICAL INFORMATION INDICATIVE OF AT LEAST ONE VITAL SIGN OF A SUBJECT

CROSS-REFERENCE TO PRIOR APPLICATIONS

This application is the U.S. National Phase application under 35 U.S.C. § 371 of International Application No. PCT/EP2019/056914, filed on Mar. 20, 2019, which claims the benefit of 1.8164137.4, filed on Mar. 27, 2018. These applications are hereby incorporated by reference herein.

FIELD OF THE INVENTION

The present invention relates to a device, system and method for extracting physiological information indicative of at least one vital sign of a subject. Further, the present invention relates to a device for obtaining detection signals allowing to extract physiological information indicative of at least one vital sign of a subject.

BACKGROUND OF THE INVENTION

Vital signs of a person, for example the heart rate (HR), the respiration rate (RR) or the (peripheral or pulsatile) blood oxygen saturation (SpO2; it provides an estimate of the arterial blood oxygen saturation SaO2), serve as indicators of the current state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that the blood absorbs light more than the surrounding tissue, so variations in blood volume with every heartbeat affect the transmission or reflectance correspondingly. Besides information about the pulse rate (heart rate), a PPG waveform (also called PPG signal) can comprise information attributable to further physiological phenomena such as the respiration. By evaluating the transmittance and/or reflectance at different wavelengths (typically red and infrared), the blood oxygen saturation can be determined.

Conventional pulse oximeters (also called contact PPG device herein) for measuring the pulse rate and the (arterial) blood oxygen saturation of a subject are attached to the skin of the subject, for instance to a fingertip, earlobe or forehead. Therefore, they are referred to as 'contact' PPG devices. Although contact PPG is basically regarded as a non-invasive technique, contact PPG measurement is often experienced as being unpleasant and obtrusive, since the pulse oximeter is directly attached to the subject and the cables limit the freedom to move and might hinder a workflow.

Non-contact, remote PPG (rPPG) devices (also called camera-based devices or video health monitoring devices) for unobtrusive measurements have been proposed in the last decade. Remote PPG utilizes light sources or, in general, radiation sources, disposed at a distance from the subject of interest. Similarly, a detector, e.g. a camera or a photodetector, can be disposed at a distance from the subject of interest. Therefore, remote photoplethysmographic systems and devices are considered unobtrusive and well suited for medical as well as non-medical everyday applications.

Using the PPG technology, vital signs can be measured. Vital signs are revealed by minute light absorption changes in the skin caused by the pulsating blood volume, i.e. by periodic color changes of the human skin induced by the blood volume pulse. As this signal is very small and hidden in much larger variations due to illumination changes and motion, there is a general interest in improving the fundamentally low signal-to-noise ratio (SNR). There still are demanding situations, with severe motion, challenging environmental illumination conditions, or strict accuracy requirements, where an improved robustness and accuracy of the vital sign measurement devices and methods is required, particularly for the more critical healthcare applications.

Video Health Monitoring (to monitor or detect e.g. heart rate, respiration rate, SpO2, actigraphy, delirium, etc.) is a promising emerging field. Its inherent unobtrusiveness has distinct advantages for patients with fragile skin, or in need of long-term vital signs monitoring, such as NICU patients, patients with extensive burns, mentally-ill patients that remove contact-sensors, or COPD patients who have to be monitored at home during sleep. In other settings such as in a general ward or emergency room, the comfort of contact-less monitoring is still an attractive feature.

The measurement of one of the important vital signs, the blood oxygen saturation (SpO2), has recently shown to be feasible with camera-based rPPG. SpO2 measurements require an accurate detection of relative pulsatilities, i.e. the normalized amplitude of the pulsatile signal (AC/DC) in different wavelength channels. There are two major threats to the accuracy in remote measurement. The first is that the pulsatilities are low compared to the noise, while the second is that ballistocardiographic (BCG) motion modifies the relative pulsatilities in each channel.

Next to oxygen saturation, the saturation of other arterial blood gasses and blood species, e.g. HBCO, MetHB, HBCO2, bilirubin, may be obtained using the same (somewhat adapted) technique, and suffer from the same threat that the current invention aims to solve. The arterial blood components are selected with this technique because only the arterial blood is assumed to pulsate at the rhythm of the cardiac activity. It is hypothesized that, similarly, the respiratory cycle induces volume variations in the venous system, implying that the relative strength of the pulsations at the respiratory rhythm in different wavelengths may be used to analyze the venous blood components, e.g. to estimate the venous oxygen saturation (SvO2).

Hence, while being a promising new field, many challenges have to be overcome. Designing the system to be robust to movements of the patient is currently one of the main challenges. One of these challenges is to achieve motion robust SPO2 measurement with a vital signs camera as well as to obtain an improved motion robust pulse- and respiratory-signal, an improved pulse- and respiratory-rate, and e.g. a robust CO-level and an improved serum bilirubin estimation (i.e. essentially all PPG-based information shall be made more robust).

US 2016/0120482 A1 discloses a device, system and a method for extracting physiological information indicative of at least one vital sign of a subject from detected electromagnetic radiation reflected from the subject. The device comprises an input interface for receiving a data stream of detection data derived from detected electromagnetic radiation reflected from a skin region of a subject, wherein the detected electromagnetic radiation is detected by a polarized radiation detector, while the polarization angle of the polarized radiation detector is changed, a PPG extraction unit for extracting a photoplethysmographic, PPG, signal from said detection data, a signal quality determination unit for determining quality metrics from said PPG signal for different settings of the polarization angle of the polarized radiation detector, a selection unit for selecting the optimum quality metric value from the determined quality metrics and for generating polarization control information for use by said polarized radiation detector for setting the polarization angle to an angle value, at which said optimum quality metric value was obtained, for subsequent detection of radiation, and a processor for deriving physiological information indicative of at least one vital sign from the PPG signal.

In conclusion, there is a need for an improved device, system and method for determining at least one vital sign of a subject to obtain results with higher reliability even in case of noise and/or motion.

SUMMARY OF THE INVENTION

It is an object of the present invention to provide a device, system and method for extracting physiological information indicative of at least one vital sign of a subject, by which results with higher reliability, even in case of noise and/or motion, can be achieved.

In a first aspect of the present invention a device is presented comprising:

a pre-treatment unit configured to derive at least three detection signals from electromagnetic radiation reflected from a skin region of a subject, wherein at least two detection signals comprise wavelength-dependent reflection information in a different wavelength channel and at least two detection signals comprise reflection information in different polarization channels having different polarization directions, wherein the pre-treatment unit is further configured to derive two of the at least three detection signals comprising wavelength-dependent reflection information in the same wavelength channel but in different polarization channels and/or to derive one of the at least three detection signals as a difference detection signal representing the difference between first reflection information in a first wavelength channel and a first polarization channel having a first polarization direction and second reflection information in the first wavelength channel and a second polarization channel having a second polarization direction different from the first polarization direction, a pulse signal computation unit configured to compute at least two pulse signals from said at least three detection signals using different given signature vectors, wherein for the computation of each pulse signal a different given signature vector is used, wherein a given signature vector represents expected relative pulsatilities of the respective pulse signal in the at least three detection signals, wherein the computation of a pulse signal involves computing a weighted combination of the at least three detection signals using weights resulting in a pulse signal for which the products with the original detection signals equals the relative pulsatilities as represented by the respective signature vector, a quality indicator computation unit configured to compute quality indicator values for said pulse signals indicating a characteristic of the respective pulse signal, and a processing unit configured to derive physiological information indicative of at least one vital sign from the signature vector that results in the pulse signal with the best quality indicator value and/or from said pulse signal with the best quality indicator value itself.

In a further aspect of the present invention a system is presented comprising:

a receiver configured to receive electromagnetic radiation reflected from a skin region of a subject, and a device as disclosed herein for extracting physiological information indicative of at least one vital sign of a subject from the received electromagnetic radiation.

In yet a further aspect of the present invention, there is provided a corresponding method.

Preferred embodiments of the invention are defined in the dependent claims. It shall be understood that the claimed method and system have similar and/or identical preferred embodiments as the claimed device, in particular as defined in the dependent claims and as disclosed herein.

Generally, a PPG signal results from variations of the blood volume in the skin. Hence, the variations give a characteristic pulsatility "signature" when viewed in different spectral components of the reflected/transmitted light. This "signature" is basically resulting as the contrast (difference) of the absorption spectra of the blood and that of the blood-less skin tissue. If the detector, e.g. a camera or sensor, has a discrete number of color channels, each sensing a particular part of the light spectrum, then the relative pulsatilities in these channels can be arranged in a "signature vector", also referred to as the "normalized blood-volume vector", PBV. It has been shown in G. de Haan and A. van Leest, "Improved motion robustness of remote-PPG by using the blood volume pulse signature", Physiol. Meas. 35 1913, 2014, which is herein incorporated by reference, that, if this signature vector is known, then a motion-robust pulse signal extraction on the basis of the color channels and the signature vector is possible. For the quality of the pulse signal, it is essential though that the signature vector is accurate, as otherwise the known methods mixes noise into the output pulse signal in order to achieve the prescribed correlation of the pulse vector with the normalized color channels as indicated by the signature vector.

Details of the PBV method and the use of the normalized blood volume vector (called "predetermined index element having a set orientation indicative of a reference physiological information") have also been described in US 2013/0271591 A1, whose details are also herein incorporated by reference, as well as WO 2017/121834 A1.

The characteristic wavelength-dependency of the PPG signal varies when the composition of the blood changes. Particularly, the oxygen saturation of the arterial blood has a strong effect on the light absorption in the wavelength range between 620 nm and 780 nm. This changing signature for different SpO2 values leads to relative PPG pulsatility that depends on the arterial blood oxygen saturation. This dependency can be used to realize a motion-robust remote SpO2 monitoring system that has been named adaptive PBV method (APBV) and is described in detail in M. van Gastel, S. Stuijk and G. de Haan, "New principle for measuring arterial blood oxygenation, enabling motion-robust remote monitoring", Nature Scientific Reports, November 2016. The description of the details of the APBV method in this document is also herein incorporated by reference.

The PBV method gives the cleanest pulse signal when the PBV vector, reflecting the relative pulsatilities in the different wavelength channels is accurate. Since this vector depends on the actual SpO2 value, testing the PBV method with different PBV vectors, corresponding to a range of SpO2 values, the SpO2 value results as the one corresponding to the PBV vector giving the pulse-signal with the highest SNR.

According to the known PBV method and APBV method the motion robustness may be reduced when the PBV vector becomes more similar to the 1-vector (i.e. in case of equal pulsatilities in all wavelengths, similar to what motion induces). This may happen when the SpO2 value drops to low values. Motion robustness still exists, but is reduced compared to the motion robustness given in case of higher SpO2 values.

The present invention is based on the idea to provide an further adaptation of the ABPV method such that the signature includes a channel that always has a low pulsatility, i.e. even when the SpO2 value is low. Suitable wavelengths do not naturally exist, but it is proposed to use polarized light and a camera in which for at least one wavelength two channels are available with different polarization (i.e. different polarization direction, e.g. one having a parallel polarization and the other one having a cross polarization). Further, a difference channel may be used that has largely suppressed the pulsatile PPG signal and only contains the motion-induced distortions. Adding an always low-pulsatile channel to the system, or replacing an existing channel with such a low-pulsatile channel solves the above described problem of reduced motion robustness.

The approach using the PBV or APBV method according to the present invention may also be understood as a quality guided walk along a defined line in color space, where the line depends on the choice of optical filters (wavelengths). This line may be curved, i.e. may be a line-segment on a unit-sphere. This automatically occurs when the PBV signature vectors all have unit length (i.e. they lie on a unit sphere). The signature vector is dynamically adapted in the color space to further reduce the influence of motion in each specific measurement.

There exist different options of how to derive the various detection signals in the various polarization channels and the various wavelength channels.

According to one embodiment, said pre-treatment unit comprises a polarization unit configured to apply a first polarization on the received electromagnetic radiation to generate first polarized radiation and to apply a second polarization, which is different from the first polarization, or no polarization on the received electromagnetic radiation to generate second polarized or non-polarized radiation, and a sensor unit configured to derive at least one detection signal from the first polarized radiation in a first wavelength channel and to derive at least two detection signals from the second polarized or non-polarized radiation in the first wavelength channel and in a second wavelength channel. In this embodiment, the received radiation is first polarized before then split into different wavelength channels. The sensor unit may comprise a filter unit configured to filter the differently polarized radiation to obtain the detection signals in the respective wavelength channels.

According to an alternative embodiment, said pre-treatment unit comprises a filter unit configured to filter the received electromagnetic radiation to generate first filtered radiation in a first wavelength channel and second filtered radiation in a second wavelength channel, a polarization unit configured to apply a first polarization on the first filtered radiation to generate first polarized radiation and to apply a second polarization, which is different from the first polarization, or no polarization on the first filtered radiation and on the second filtered radiation to generate second polarized or non-polarized radiation and third polarized or non-polarized radiation, and a sensor unit configured to derive at least one detection signal from each of the first polarized radiation and the second and third polarized or non-polarized radiation. In this embodiment, the received radiation is first split into different wavelength channels before the different polarizations are applied.

The choice of one of these embodiments may be determined by the relative price of wavelength-selective filters and polarizers. It may e.g. be preferred to put the most expensive first and then split the optical path further with cheaper filters.

Said pre-treatment unit may be configured to derive at least two detection signals comprising reflection information in two different polarization channels having orthogonal polarization directions, preferably a first detection signal comprising reflection information in a first polarization channel having a first polarization direction, which is parallel to the polarization direction of polarized electromagnetic radiation used for illuminating the skin region of the subject, and a second detection signal comprising reflection information in a second polarization channel having a second polarization direction, which is orthogonal to the polarization direction of polarized electromagnetic radiation used for illuminating the skin region of the subject. In this way it is possible to select the scattered reflection component of the received radiation by suppressing the specular reflection component using a cross-polarization direction. Further, a parallel polarizer passes the specular reflection. Since the diffuse (specular) reflection contains all polarization directions without preferential phase, the absolute pulsatility in a channel does not depend on the polarization direction. Consequently, the difference of a sensor signal equipped with a parallel polarizer and a sensor signal with an orthogonal polarizer contains hardly any scattered reflection, but only specular reflection which is non-pulsatile, i.e. a desired low-pulsatile channel is thus provided for use in the PBV or APBV method.

Various combinations of detection signals and polarization/wavelength channels can be exploited in various preferred embodiments.

In one embodiment said pre-treatment unit is configured to derive
a first detection signal comprising reflection information in a first wavelength channel and a first polarization channel having a first polarization direction, which is parallel to the polarization direction of polarized electromagnetic radiation used for illuminating the skin region of the subject,
a second detection signal comprising reflection information in the first wavelength channel and a second non-polarized polarization channel, and
a third detection signal comprising reflection information in a second wavelength channel, different from the first wavelength channel, and the second non-polarized polarization channel.

In another embodiment said pre-treatment unit is configured to derive
a first detection signal comprising reflection information in a first wavelength channel and a first polarization channel having a first polarization direction, which is parallel to the polarization direction of polarized electromagnetic radiation used for illuminating the skin region of the subject,
a second detection signal comprising reflection information in the first wavelength channel and a second polarization channel having a second polarization direction, which is orthogonal to the polarization direction of polarized electromagnetic radiation used for illuminating the skin region of the subject, and a third detection signal comprising reflection information in a second wavelength channel, different from the first wavelength channel, and the second polarization channel.

Hereby, said pre-treatment unit may further be configured to derive a fourth detection signal comprising reflection information in a third wavelength channel, different from the first and second wavelength channels, and the second polarization channel. This further improves the reliability of the final vital sign.

In still another embodiment said pre-treatment unit and/or said pulse signal computation unit is configured to derive a difference detection signal representing the difference between first reflection information in a first wavelength channel and a first polarization channel having a first polarization direction and second reflection information in the first wavelength channel and a second polarization channel having a second polarization direction different from the first polarization direction, and said pulse signal computation unit is configured to use said difference detection signal as one of the detection signals for computing the at least two pulse signals. This difference detection signal (i.e. difference channel) has a very low pulsatility, regardless the selected wavelength or SpO2 level, and thus keeps the angle of the PBV vector with the vector [1 1 1] large by providing a channel with always low pulsatility.

Further, in an embodiment said pulse signal computation unit is configured to use a fixed or adaptive set of different signature vectors and said processing unit is configured to filter a time sequence of signature vectors that resulted in the pulse signal with the best quality indicator value to obtain a filtered signature vector from which the physiological information is derived, wherein said time sequence of signature vectors is obtained from pulse signals and quality indicators computed for successive time windows of said at least two detection signals. According to one option of this embodiment the set of different signature vectors is fixed, i.e. each signature vector corresponds to a discrete vital signs value, e.g. a SpO2 value (in a range between 60% and 100%, e.g. covered by 10 signature vectors). Further, the filtered signature vector (having an increased resolution, e.g. SpO2 resolution) is used to derive the output vital sign, using the fact that the signature vector one-on-one corresponds to vital signs value, e.g. an SpO2 value. According to another option of this embodiment the set of different signature vectors is an adaptive set of different signature vectors, in particular in case a recursive, rather than a parallel, optimization of the signature vector is made.

Still further, a signature adaptation unit may be provided for adapting one or more of the different signature vectors in a direction that depends on which pulse signal yields the best quality indicator value. According to this embodiment a signature value is adapted (i.e. updated) in a direction (e.g. an update value is increased or decreased) that depends on which pulse signal (computed using one of the signature values) yields the best quality indicator value. Hence, a recursive/iterative option is used according to this embodiment. Generally, the adaptive set of signature vectors may contain only two signature vectors, but more is possible.

Thus, this embodiment provides an adaptation scheme of the signature vector in a PPG sensor as disclosed in the above cited paper of de Haan and van Leest such that the signature automatically converges to the correct signature vector. On top of improving the motion and noise robustness of the pulse signal, a further advantage is that the momentary signature vector carries all relevant information concerning the composition of the blood (e.g. of SpO2, CO, CO2, bilirubin). E.g., the SpO2 is determined by the signature vector of that moment. In case of the parallel implementation, the Spo2 is determined by the selected (i.e. the momentary) signature vector.

In case of partly adapting the set of signature values the recursive/iterative option may be extended with a fixed signature vector that is always tested. The set may thus contain two adapted signature vectors, and e.g. one up to three fixed signature vectors that may speed up recovery if the recursive approach got "off-track", e.g. by excessive noise.

In case of partly adapting the set of signature values the recursive/iterative option may be extended with a fixed signature vector that is always tested. The set may thus contain two adapted signature vectors, and e.g. one up to three fixed signature vectors that may speed up recovery if the recursive approach got "off-track", e.g. by excessive noise. Preferably, all possible signature vectors are tested simultaneously rather than recursively/iteratively.

In another preferred embodiment said signature adaptation unit is configured to use a reference signature vector to obtain at least two signature vectors based on said quality indicator values and wherein said pulse signal computation unit is configured to compute said pulse signals from said detection signals for said at least two signature vectors, wherein a ratio between a pulse signal and said at least two detection signals is determined by the corresponding signature vector. The reference signature vector is preferably fixed and predetermined. It may e.g. be measured once for a given configuration (camera, light-source) on a healthy individual (i.e. with a healthy SpO2 around 97%). It is also possible to use a phantom for this. The phantom can be a computer monitor displaying a surface with the color variations typically seen in healthy skin. The computer monitor can be an array of EM-radiation emitters (pixels) that displays a surface with EM-radiation variations in the selected wavelength channels similar to healthy skin. The reference signature vector does not have to correspond though to the signature vector of a healthy individual. It is also possible to take a vector that corresponds to another SpO2 value, e.g. of 80%. As long as the reference signature vector is within the range that may occur (between 70% and 100% SpO2), it may serve as an initial estimate and the method according to the present invention will converge towards the actual signature value of the subject monitored.

The above described embodiment leads to a well working system, and the reference (REF) signature vector may be chosen to correspond with the signature of an SpO2 value of e.g. 85% (more or less in the middle of the range). The REF vector may, however, also be outside this range. A required range, e.g. between 100% and 75%, or between 110% and 70%, shall, however, be covered. This can be achieved e.g. with the following equation, which describes the candidate signature vectors: REF+n×UPD, where the update vector UPD is a vector describing the difference between e.g. 100% and 75% with n in steps e.g. of 1/25 (which provides a resolution of 1% before filtering the signature-sequence).

The reference signature vector may even be at an impossible SpO2 level, e.g. 120%×REF+n×UPD, wherein 0<n<30 needs not to be chosen, but it is also possible to choose 20<n<50 (assuming 1% SpO2 accuracy in this example).

Hence, the REF vector can be modified with (fractions, or multiples of) the UPD vector to obtain the signature vectors corresponding to SpO2 values different from that the REF vector corresponds to.

Preferably, said signature adaptation unit is configured to adapt a reference normalized blood volume pulse vector as reference signature vector to obtain the at least two signature vectors.

There are different options to determine the quality indicator values. In an embodiment said quality indicator computation unit is configured to compute the spectrum of normalized pulse signals, in particular over a sliding time window, and to use an amplitude of the highest peak in a range, in particular of typical pulse frequencies, as the quality indicator for said pulse signal. In another embodiment, said quality indicator computation unit is configured to compute pulse signals in a sliding time window and to define an amplitude of the highest peak in the range of the pulse frequencies of the magnitude spectrum, divided by the energy over the full frequency range (which may also be the range of possible pulse frequencies), as the quality indicator for said pulse signal. In yet another embodiment, said quality indicator may use the skewness of the magnitude spectrum of the pulse signals as an indicator of their quality.

The signature adaptation unit may be configured to compare said quality indicator values to increase or decrease a counter depending on the sign of the comparison and to use the counter value together with a predetermined update vector and the reference signature vector to compute the at least two signature vectors. The update vector is generally predetermined. For instance, if a signature vector describing the relative pulsatilities in the detection signals for 100% SpO2 is used as $P_{bv}2$ and from that the signature vector $P_{bv}3$ for e.g. 80% SpO2 is subtracted, a fraction of this difference vector may be used as update vector.

The pulse signal computation unit may further be configured to add noise to one or more of the said at least two detection signals, in particular to one or more normalized and DC-free detection signals before computing said pulse signals therefrom. Adding some noise to the color channels improves the performance, in particular in case the skin area is large and there is little observation or motion-induced noise. The advantageous effect is that the estimation of all the vital signs actually profits from noise (e.g. motion) as the optimal signature is clearest in the presence of a disturbance. In a very noise-free situation, almost all signature vectors (PBVs) may lead to a clean pulse signal so that it may become hard to find the optimum.

As explained above, the present invention preferably exploits the known PBV or APBV method. In a practical implementation, said pulse signal computation unit is configured to compute said pulse signals $S_1$, $S_2$ by computing a covariance matrix $Q = C_n C_n^T$ of normalized DC-free detection signals $C_n$ over a time window and find the weights $W_x$ to compute a pulse signal $S_x = \vec{W}_x C_n$ as $\vec{W}_x = k \vec{P}_{bvx} Q^{-1}$, where k is chosen to make $\|\vec{W}_x\|=1$ and $x \in \{1, 2\}$. It shall be noted here that the weights and the PBVs are different for the two pulse signals obtained from the same detection signals $C_n$. It should be further noted that writing $Q^{-1}$ assumes that Q can be inverted. In practice a pseudo-inverse may be used, i.e. a least-mean-squares approximation of the inverse of Q in case it is not exactly invertible, accepting an imperfect (but still the best possible in LMS-sense) $Q^{-1}$).

The proposed system for extracting physiological information indicative of at least one vital sign of a subject comprises a receiver configured to receive electromagnetic radiation reflected from a skin region of a subject, and a device as described above for extracting physiological information indicative of at least one vital sign of a subject from the received electromagnetic radiation.

The receiver of the proposed system may be configured in different ways, in particular to receive detection signals at different wavelengths, preferably depending on the kind of application and the system configuration. In general, the detection signals are selected from a wavelength interval between 300 nm and 1000 nm, in particular represent the wavelength portions corresponding to red, green and blue light. This is particularly used when the PPG signals are obtained from image signals acquired by a (e.g. conventional) video camera and when the above mentioned principles of remote PPG are used for deriving one or more vital signs. In other embodiments infrared light may also be used in addition or instead of another color channel. For instance, for night-time applications one or more infrared wavelengths may be used in addition or alternatively.

The receiver may be configured as optical element, e.g. a lens, of an imaging unit, such as an optical sensor, a camera, e.g. a video camera, an RGB camera or web-cam.

Preferably, the system further comprises an illumination unit, such as a light source (e.g. LEDs with polarizers) configured to illuminate the skin region of the subject with linearly polarized electromagnetic radiation, in particular within the wavelength range from 300 nm to 1000 nm.

The proposed system may further comprise an output unit configured to output the vital sign. The output unit may e.g. be a user interface like a display, computer or loudspeaker. Still further, the proposed system may comprise a control unit configured to generate, based on the vital sign, an alarm control signal for controlling an alarm unit configured to issue an alarm and to output the generated alarm control signal.

According to a further aspect, the present invention is directed to a device for obtaining detection signals allowing to extract physiological information indicative of at least one vital sign of a subject. Said device comprises a receiver configured to receive electromagnetic radiation reflected from a skin region of a subject, and a pre-treatment unit configured to derive at least three detection signals from electromagnetic radiation reflected from a skin region of a subject, wherein at least two detection signals comprise wavelength-dependent reflection information in a different wavelength channel and at least two detection signals comprise reflection information in different polarization channels having different polarization directions, wherein the pre-treatment unit is further configured to derive two of the at least three detection signals comprising wavelength-dependent reflection information in the same wavelength channel but in different polarization channels and/or to derive one of the at least three detection signals as a difference detection signal representing the difference between first reflection information in a first wavelength channel and a first polarization channel having a first polarization direction and second reflection information in the first wavelength channel and a second polarization channel having a second polarization direction different from the first polarization direction. The device may e.g. be implemented as a camera or other imaging unit.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

In the following the invention will be explained by referring to the example of motion robust detection of SpO2. For other vital signs, e.g. blood components, details of the following description may need to be adapted accordingly.

Figure 1:
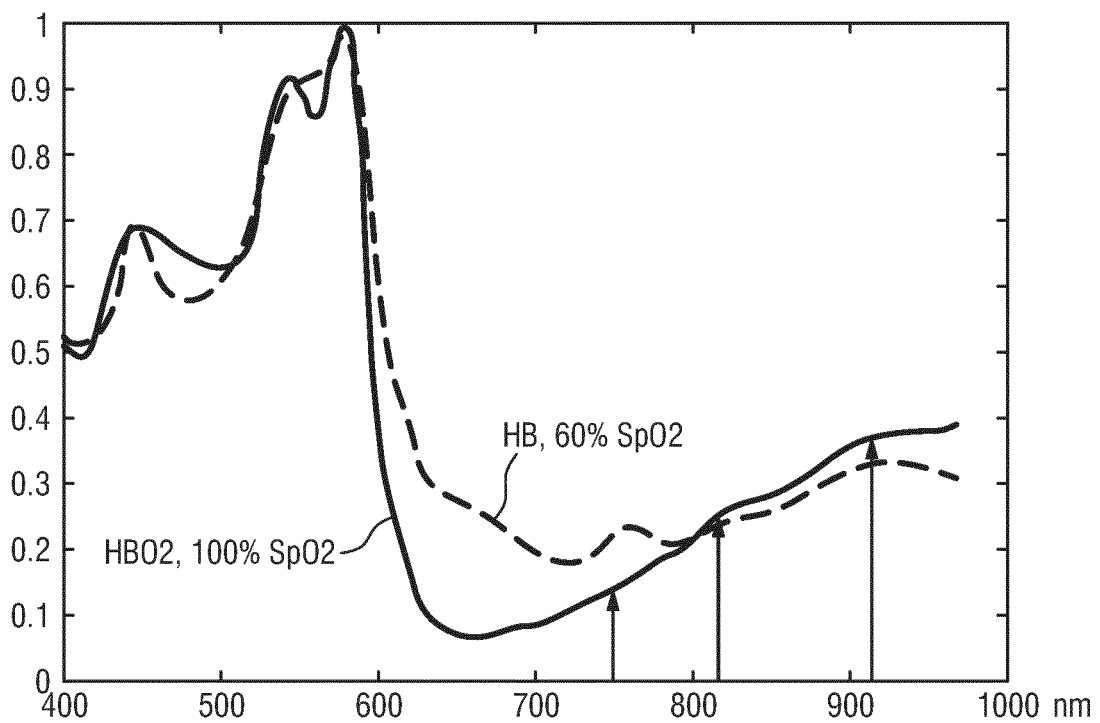
FIG. 1 shows a diagram of the absorption spectrum of blood.

FIG. 1 shows a diagram of the absorption spectrum of blood. As shown in FIG. 1, for a healthy individual, with an arterial blood oxygenation level close to 100%, the relative pulsatility, i.e. AC/DC of the reflected light from the skin, is known for individual wavelengths. For example, the relative pulsatility is known at three wavelengths, 760 nm, 810 nm and 905 nm (a good choice of wavelengths used in recent SpO2 monitoring, striking a balance between SpO2 sensitivity and invisibility. In case invisibility of the EM (electromagnetic) radiation source is no issue, the 760 nm is preferably swapped with 660 nm). The three relative pulsatilities can be written as the components of a so-called unit length normalized blood volume pulse vector (also called signature vector) PBV. It is the essence of the PBV-method for motion-robust pulse extraction that the stable character of PBV can be used to distinguish color variations caused by blood volume change from variations due to alternative causes.

If a camera or sensor samples the spectrum shown in FIG. 1, e.g. around 760 nm, 810 nm and 905 nm, the "signature" vector, PBV, has three components, and they depend on the SpO2. If the oxygenation level of the arterial blood drops, at some point (around 75-80% oxygenation level) the three components of the PBV vector become more similar. Since motion also induces variations that are identical for all components, motion-robustness of SpO2 measurement is significantly reduced for low SpO2.

In the following some basic considerations with respect to the PBV method shall be briefly explained, using RGB-wavelength channels as an example.

The beating of the heart causes pressure variations in the arteries as the heart pumps blood against the resistance of the vascular bed. Since the arteries are elastic, their diameter changes in synchrony with the pressure variations. These diameter changes occur even in the smaller vessels of the skin, where the blood volume variations cause a changing absorption of the light.

The unit length normalized blood volume pulse vector (also called signature vector) is defined as PBV, providing the relative PPG-strength in the red, green and blue camera signal, i.e.

$$\vec{P}_{bv} = \frac{[\sigma(\vec{R}_n), \sigma(\vec{G}_n), \sigma(\vec{B}_n)]}{\sqrt{\sigma^2(\vec{R}_n) + \sigma^2(\vec{G}_n) + \sigma^2(\vec{B}_n)}}$$

with σ indicating the standard deviation.

To quantify the expectations, the responses $H_{red}(w)$, $H_{green}(w)$ and $H_{blue}(w)$ of the red, green and blue channel, respectively, were measured as a function of the wavelength w, of a global-shutter color CCD camera, the skin reflectance of a subject, $\rho_s(w)$, and used an absolute PPG-amplitude curve PPG(w). From these curves, shown e.g. in FIG. 2 of the above cited paper of de Haan and van Leest, the blood volume pulse vector PBV is computed as:

$$\hat{P}_{bv}^T = \begin{bmatrix} \dfrac{\int_{w=400}^{700} H_{red}(w)I(w)PPG(w)\,dw}{\int_{w=400}^{700} H_{red}(w)I(w)\rho_s(w)\,dw} \\[1em] \dfrac{\int_{w=400}^{700} H_{green}(w)I(w)PPG(w)\,dw}{\int_{w=400}^{700} H_{green}(w)I(w)\rho_s(w)\,dw} \\[1em] \dfrac{\int_{w=400}^{700} H_{blue}(w)I(w)PPG(w)\,dw}{\int_{w=400}^{700} H_{blue}(w)I(w)\rho_s(w)\,dw} \end{bmatrix}$$

which, using a white halogen illumination spectrum I(w), leads to a normalized PBV=[0.27, 0.80, 0.54].

The blood volume pulse predicted by the used model corresponds reasonably well to an experimentally measured normalized blood volume pulse vector, PBV=[0.33, 0.78, 0.53] found after averaging measurements on a number of subjects under white illumination conditions. Given this result, it was concluded that the observed PPG-amplitude, particularly in the red, and to a smaller extent in the blue camera channel, can be largely explained by the crosstalk from wavelengths in the interval between 500 and 600 nm. The precise blood volume pulse vector depends on the color filters of the camera, the spectrum of the light and the skin-reflectance, as the model shows. In practice, the vector turns out to be remarkably stable though given a set of wavelength channels (the vector will be different in the infrared compared to RGB-based vector).

It has further been found that the relative reflectance of the skin, in the red, green and blue channel under white illumination does not depend much on the skin-type. This is likely because the absorption spectra of the blood-free skin is dominated by the melanin absorption. Although a higher melanin concentration can increase the absolute absorption considerably, the relative absorption in the different wavelengths remains the same. This implies an increase of melanin darkens the skin but hardly changes the normalized color of the skin. Consequently, also the normalized blood volume pulse PBV is quite stable under white illumination. In the infrared wavelengths, the influence of melanin is further reduced as its maximum absorption occurs for short wavelengths (UV-light) and decreases for longer wavelengths.

The main reason the PBV vector is not affected much by the melanin is that melanin is in the epidermis and therefore acts as an optical filter on both the AC and the DC. Hence, it may reduce the pulsatility, but at the same time also the DC value of the reflection. Hence the AC/DC (relative pulsatility) does not change at all.

The stable character of PBV can be used to distinguish color variations caused by blood volume change from variations due to alternative causes, i.e. the stable PBV can be used as a "signature" of blood volume change to distinguish their color variations. The known relative pulsatilities of the color channels PBV can thus be used to discriminate between the pulse-signal and distortions. The resulting pulse signal S using known methods can be written as a linear combination (representing one of several possible ways of "mixing") of the individual DC-free normalized color channels:

$$S = WC_n$$

with $WW^T = 1$ and where each of the three rows of the 3×N matrix $C_n$ contains N samples of the DC-free normalized red, green and blue channel signals $R_n$, $G_n$ and $B_n$, respectively, i.e.:

$$\vec{R}_n = \frac{1}{\mu(\vec{R})}\vec{R} - 1, \vec{G}_n = \frac{1}{\mu(\vec{G})}\vec{G} - 1, \vec{B}_n = \frac{1}{\mu(\vec{B})}\vec{B} - 1.$$

Here the operator μ corresponds to the mean. Key difference between the different methods is in the calculation of the weighting vector W. In one method, the noise and the PPG signal may be separated into two independent signals built as a linear combination of two color channels. One combination approximated a clean PPG signal, the other contained noise due to motion. As an optimization criterion the energy in the pulse signal may be minimized. In another method a linear combination of the three color channels may be used to obtain the pulse signal.

The PBV method generally obtains the mixing coefficients using the blood volume pulse vector as basically described in US 2013/271591 A1 and the above cited paper of de Haan and van Leest. The best results are obtained if the band-passed filtered versions of $R_n$, $G_n$ and $B_n$ are used. According to this method the known direction of PBV is used to discriminate between the pulse signal and distortions. This not only removes the assumption (of earlier methods) that the pulse is the only periodic component in the video, but also eliminates assumptions on the orientation of the distortion signals. To this end, it is assumed as before that the pulse signal is built as a linear combination of normalized color signals. Since it is known that the relative amplitude of the pulse signal in the red, green and blue channel is given by PBV, the weights, $W_{PBV}$, are searched that give a pulse signal S, for which the correlation with the color channels $R_n$, $G_n$, and $B_n$ equals PBV $$\vec{S}C_n^T = k\vec{P}_{bv} \Leftrightarrow \vec{W}_{PBV}C_nC_n^T = k\vec{P}_{bv}, \quad (1)$$

and consequently the weights determining the mixing are determined by $$\vec{W}_{PBV} = k\vec{P}_{bv}Q^{-1} \text{ with } Q = C_nC_n^T, \quad (2)$$

and the scalar k is determined such that $W_{PBV}$ has unit length. It is concluded that the characteristic wavelength dependency of the PPG signal, as reflected in the normalized blood volume pulse, PBV, can be used to estimate the pulse signal from the time-sequential RGB pixel data averaged over the skin area. This algorithm is referred to as the PBV method.

In other words, the weights indicate how the detection signals should be (linearly) combined in order to extract a pulse signal from the detection signals. The weights are unknown and need to be computed/selected.

The signature vector (PBV vector) represent the given (known or expected) relative pulsatilities in different wavelength channels (i.e. the detection signals), caused by the absorption spectrum of the blood and the penetration of light into the skin (if photons are more absorbed by blood, a volume change of blood leads to a larger signal than when the blood is nearly transparent). With this knowledge, and the observed data (i.e. the detection signals) the weights (e.g. a weight vector) can be determined. The resulting weights are data dependent, i.e. depend on the detection signals.

Since the pulse signal has a different ratio AC/DC (this is also called the relative signal strength/pulsatility) in each wavelength channel, it can be seen that the spectrum shows the pulse peak in the spectrum with different peak values for the different colors. This spectrum is the result of a Fourier analysis, but it basically means that if a sinusoid having the pulse frequency is correlated (multiplied) with the detection signals (RGB in the example, NIR-wavelengths for SpO2), exactly the peak values in the spectrum are obtained, which by definition are called the signature vector (PBV vector): these peak values are the relative strength of the normalized amplitudes of the pulse signal in the different detection signals.

The consequence of this is that a clean pulse signal S can be obtained (assuming the pulse signal is the result of a weighted sum of the detection signals), using this prior knowledge (i.e. the signature vector). One option to do this is to compute an inversion of a covariance matrix Q of the normalized detection signals $C_n$. Hence, the weights W to linearly mix the detection signals in order to extract the pulse signal S can be computed from the covariance matrix of the detection signals in the current analysis window (Q, which is data dependent, i.e. changes continuously over time), using the constant signature vector PBV.

It is recognized that e.g. in the NIR-light spectrum, particularly between 620 and 770 nm, the blood absorption spectrum changes depending on the SpO2 level. For this reason it is proposed to extract the pulse signal with different signature vectors (different PBV vectors), where each PBV vector is chosen to correspond with the relative pulsatilities in the detection signals for a particular vital sign value, e.g. an SpO2 value. Since the extracted pulse signal quality depends on the correctness of the PBV vector, the different extracted pulse signals will have a different quality. By selecting the best quality pulse signal, the vital sign value (e.g. SpO2 value) can be derived from the signature vector that caused this favorable pulse signal.

In another embodiment the APBV method is used to extract an SpO2 value from two or more different combinations of three wavelength channels, e.g. from [λ1, λ2], from [λ1, λ3], and/or from [λ1, λ2, λ3]. In the following some basic considerations with respect to the APBV method shall be briefly explained.

Instead of extracting features from the PPG waveforms, APBV determines SpO2 indirectly based on the signal quality of the pulse signals extracted with SpO2 'signatures'. This procedure can mathematically be described as:

$$SpO_2 = \underset{SpO_2 \in SpO_2}{\operatorname{argmax}} SNR\left(\frac{\vec{W}_{PBV}}{k\vec{P}_{bv}(SpO_2)[C_nC_n^T]^{-1}C_n}\right), \quad (3)$$

where $C_n$ contains the DC-normalized color variations and scalar k is chosen such that $\vec{W}_{PBV}$ has unit length. The SpO2 signatures compiled in $\vec{P}_{bv}$ can be derived from physiology and optics. Assuming identical cameras the PPG amplitudes of N cameras can be determined by:

$$\vec{P}_{bv} = \left\| \begin{pmatrix} \left(\frac{AC}{DC}\right)^1 \\ \left(\frac{AC}{DC}\right)^2 \\ \vdots \\ \left(\frac{AC}{DC}\right)^N \end{pmatrix} \right\| = \left\| \begin{pmatrix} \frac{\int_\lambda I(\lambda)F^1(\lambda)C(\lambda)PPG(\lambda)d\lambda}{\int_\lambda I(\lambda)F^1(\lambda)C(\lambda)\rho_s(\lambda)d\lambda} \\ \frac{\int_\lambda I(\lambda)F^2(\lambda)C(\lambda)PPG(\lambda)d\lambda}{\int_\lambda I(\lambda)F^2(\lambda)C(\lambda)C(\lambda)\rho_s(\lambda)d\lambda} \\ \vdots \\ \frac{\int_\lambda I(\lambda)F^N(\lambda)C(\lambda)PPG(\lambda)d\lambda}{\int_\lambda I(\lambda)F^N(\lambda)C(\lambda)\rho_s(\lambda)d\lambda} \end{pmatrix} \right\| \quad (4)$$

Here the PPG amplitude spectrum, $PPG(\lambda)$, can be approximated by a linear mixture of the light absorption spectra from the two most common variants of the main chromophore in arterial blood, hemoglobin; oxygenated (HbO2) and reduced (Hb):

$$PPG(\lambda) \approx \epsilon_{Hb}(\lambda)C_{Hb} + \epsilon_{HbO_2}(\lambda)C_{HbO_2} = \quad (5)$$
$$(1 - SaO_2)\epsilon_{Hb}(\lambda) + SaO_2\epsilon_{HbO_2}(\lambda) = \epsilon_{Hb}(\lambda) + SaO_2[\epsilon_{HbO_2}(\lambda) - \epsilon_{Hb}(\lambda)],$$

where it is assumed that the optical path length differences are negligible for $600 < \lambda < 1000$ nm and $SaO_2 \in [0, 1]$. It is recognized that the wavelength-dependent effect of scattering could render this assumption invalid. When using two wavelengths, the ratio-of-ratios parameter R and the ratio of APBV parameter $\vec{P}_{bv}$ coincide. The wavelength selection may be based on three criteria: 1) the desire to measure oxygen saturation in darkness ($\lambda > 700$ nm) for clinical applications, 2) have a reasonable SpO2 contrast, and 3) wavelengths within the spectral sensitivity of the camera. The idea to use three instead of the common two wavelengths used in pulse-oximetry was motivated by the improved robustness of the SpO2 measurement by a factor of two. This can be explained by how motion affects the PPG waveforms when measured with a camera. Since motion-induced intensity variations are equal for all wavelengths, suppression of these artifacts is possible for the APBV method if the pulse signature $\vec{P}_{bv}$ is not equal to this motion signature, which can be described as a vector with equal weights.

It shall be noted that even if the pulse quality is very good, it does not always mean that the estimated SpO2 value is sufficiently reliable and can be trusted. This may particularly happen when unexpected blood-species (e.g. COHb) are available causing the SpO2 calibration curve to shift, i.e. causing a different signature vector to lead to the optimal pulse quality when using the PBV method or APBV method for pulse extraction.

It is critical in the above, that the PBV method assumes the relative pulsatilities in the wavelength channels are known, which is true if the desired vital sign information, e.g. the SpO2, were known. This however, in SpO2 monitoring, essentially is not the case since this is the parameter that is searched for. If the weights are chosen correctly, the correlation of the resulting pulse with the individual detection signals $C_n$ are exactly these relative strengths of the pulse in detection signals $C_n$. Now, if the vital sign information (e.g. the SpO2) is wrong or unknown, the result will be a pulse signal with a relatively poor SNR (i.e. a poor quality indicator).

The essence of the APBV method is to run a number of PBV methods in parallel with different PBV vector. The PBV method gives the cleanest pulse signal when the PBV vector, reflecting the relative pulsatilities in the different wavelength channels is accurate. Since this vector depends on the actual SpO2 value, testing the PBV method with different PBV vectors, corresponding to a range of SpO2 values, the SpO2 value results as the one corresponding to the PBV vector giving the pulse signal with the highest SNR.

Although the ABPV method is revolutionary in that it allows for the first time a motion robust remote SpO2 measurement, there is a weakness which limits the robustness. As can be seen from the diagram shown in FIG. 1, the relative pulsatilities in the three wavelength-channels become more similar when the oxygenation level of the blood drops. The motion robustness of the PBV method is indicated by the angle between the PBV vector and the vector [1 1 1] that corresponds to the dominant relative strength of the motion-induced signal component in the three wavelength channels. The smaller this angle, the less the motion robustness.

There are multiple reasons for the limitation to the NIR-part of the illumination spectrum. For instance, it is desired to monitor in full darkness for sleeping patients (though there are technical reasons too), so from FIG. 1 it is clear that this problem is impossible to solve by another selection of wavelengths.

Figure 2:
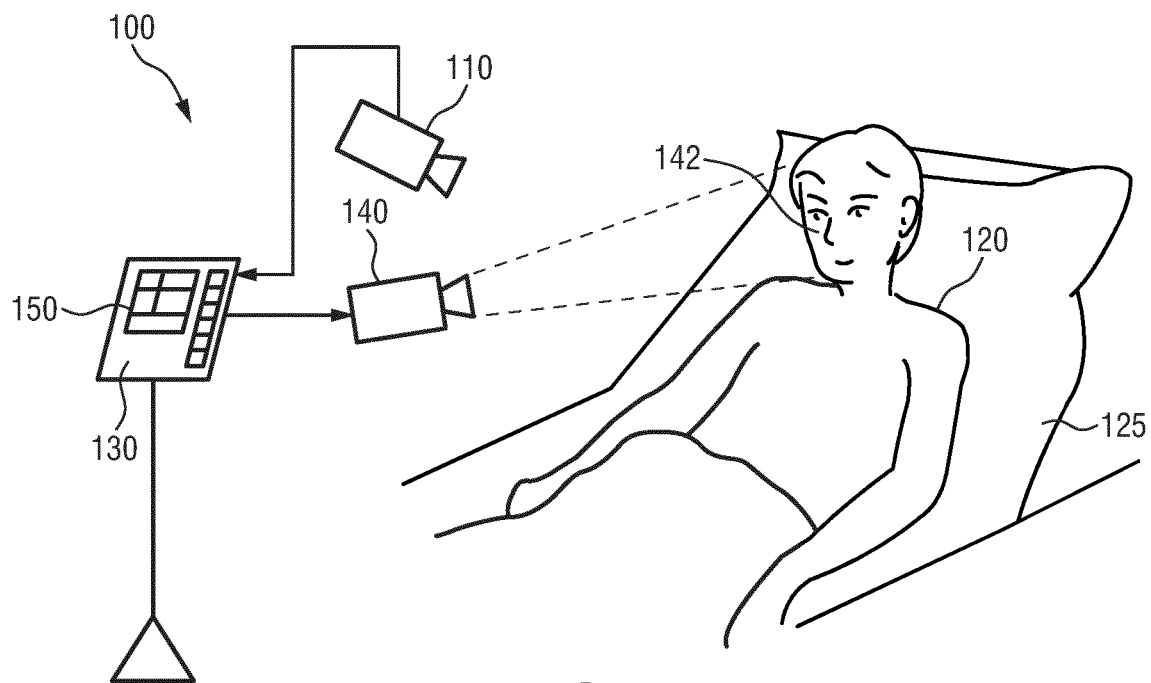
FIG. 2 shows a schematic diagram of an embodiment of a system according to the present invention.

FIG. 2 shows a schematic diagram of an embodiment of a system 100 according to the present invention. The system 100 comprises a receiver (also called detector) 110 for receiving electromagnetic radiation reflected from a skin region of a subject 120. The system 100 further comprises a device 130 for determining physiological information indicative of at least one vital sign of a subject or for determining at least one vital sign of the subject from the received electromagnetic radiation. The subject 120, in this example is a patient, lies in a bed 125, e.g. in a hospital or other healthcare facility, but may also be a neonate or premature infant, e.g. lying in an incubator, or person at home or in a different environment.

The system 100 may further optionally comprise a light source 140 (also called illumination unit), such as a lamp, for illuminating a region of interest 142 with linearly polarized electromagnetic radiation (light), such as the skin of the patient's face (e.g. part of the cheek or forehead), with light, for instance in a predetermined wavelength range or ranges (e.g. in the red, green and/or infrared wavelength range(s)) and with a predetermined polarization having a predetermined polarization direction. The light reflected from said region of interest 142 in response to said illumination is received by receiver 110, e.g. the lens of a camera or other optics in front of a sensor. In another embodiment no dedicated light source is provided, but ambient light is used for illumination of the subject 120. From the reflected light, only light in a number of desired wavelength ranges (e.g. green and red or infrared light, or light in a sufficiently large wavelength range covering at least two wavelength channels) may be detected and/or evaluated.

The device 130 is further connected to an interface 150 for displaying the determined information and/or for providing medical personnel with an interface to change settings of the device 130, the receiver 110, the light source 140 and/or any other parameter of the system 100. Such an interface 150 may comprise different displays, buttons, touchscreens, keyboards or other human machine interface means.

A system 100 as illustrated in FIG. 2 may, e.g., be located in a hospital, healthcare facility, elderly care facility or the like. Apart from the monitoring of patients, the present invention may also be applied in other fields such as neonate monitoring, general surveillance applications, security monitoring or so-called live style environments, such as fitness equipment, a wearable, a handheld device like a smartphone, or the like. The uni- or bidirectional communication between the device 130 and the interface 150 may work via a wireless or wired communication interface. Other embodiments of the present invention may include a device 130, which is not provided stand-alone, but integrated into a camera or the interface 150.

Typically, the electromagnetic radiation is in the range of 400 nm to 1000 nm for pulse, respiration and blood oxygen saturation measurement, particularly in the range of 620 nm to 920 nm. This particular range is most suitable for SpO2 measurement and is attractive for unobtrusive monitoring during sleep (darkness), but if pulse or respiratory signals are required, the visible part of the spectrum may allow a higher quality (i.e. NIR is not necessarily the preferred option in all cases). The detection signals may be acquired by a photo-sensor (array) and/or using a video camera remotely sensing the subject's skin.

Figure 3:
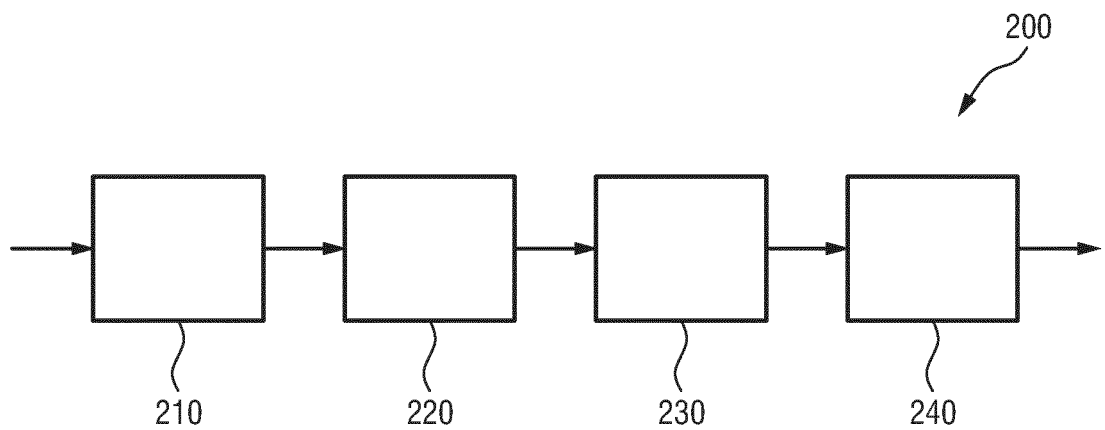
FIG. 3 shows a schematic diagram of an embodiment of a device for extracting physiological information indicative of at least one vital sign of a subject according to the present invention.

FIG. 3 shows a schematic diagram of a first embodiment of a device 200 according to the present invention for extracting physiological information indicative of at least one vital sign of a subject. The device 200 may be integrated into the receiver 110, e.g. a camera, or may partly be integrated into or combined with the receiver 110 and partly be realized by the device 130, e.g. a processor or computer.

The device 200 comprises a pre-treatment unit 210 configured to derive at least three detection signals Ci from electromagnetic radiation reflected from a skin region of a subject. At least two detection signals comprise wavelength-dependent reflection information in a different wavelength channel and at least two detection signals comprise reflection information in different polarization channels having different polarization directions. The pre-treatment unit may comprise optical elements, such as prisms, beam-splitter, dichroic mirrors, etc. and one or more sensors or detectors.

The device 200 further comprises a pulse signal computation unit 220 for computing at least two pulse signals $S_1$, $S_2$ from said at least three detection signals $C_n$ using different given signature vectors $P_{bv}1$, $P_{bv}2$. For the computation of each pulse signal a different given signature vector is used. A given signature vector represents expected relative pulsatilities of the respective pulse signal in the at least three detection signals, wherein the computation of a pulse signal involves computing a weighted combination of the at least three detection signals using weights resulting in a pulse signal for which the products with the original detection signals equals the relative pulsatilities as represented by the respective signature vector.

The device 200 further comprises a quality indicator computation unit 230 for computing quality indicator values $Q_1$, $Q_2$ for said pulse signals $S_1$, $S_2$ indicating a characteristic of the respective pulse signal.

The device 200 further comprises a processing unit 240 for deriving physiological information V indicative of at least one vital sign from the signature vector that results in the pulse signal with the best quality indicator value $Q_1$, $Q_2$ and/or from said pulse signal itself.

The units 220, 230 and 240 of the device 200 may be comprised in one or multiple digital or analog processors depending on how and where the invention is applied. The different units may completely or partly be implemented in software and carried out on a personal computer connected to one or more detectors. Some or all of the required functionality may also be implemented in hardware, e.g. in an application specific integrated circuit (ASIC) or in a field programmable gate array (FPGA). In an embodiment, these units are part of the device 130 of the system 100. In another embodiment, these units are integrated into the receiver 110.

The pre-treatment unit 210, in particular any optical elements and any sensing elements, are integrated into or combined with the receiver 110, e.g. may together form an optical camera.

The present invention exploits the finding that the electromagnetic radiation (light) reflected from the skin has two components: the surface reflection component and the component that originates from scattering processes underneath the surface in the translucent skin tissue. Only the scattered component is actually modulated by the blood-volume changes that occur inside the tissue, while the surface (or specular) reflection component remains unmodulated by the blood volume variations (it may be modulated by motion).

One idea of the present invention is that only the specular reflection preserves the polarization direction of the light, whereas the scattered (diffuse) reflection component changes it in all possible directions. By using e.g. polarized light, and wavelength channels registered with a sensor that e.g. has a second polarizer in front of its surface, not only (about half of) the scattered reflection can be selected by suppressing the specular reflection component using a cross-polarization direction, but also the specular reflection can be selected with a parallel polarizer which passes the specular reflection plus (about the other half of) the scattered reflection.

Since the diffuse reflection contains all polarization directions without preferential phase, the absolute pulsatility in a channel does not depend on the polarization direction (about half the scattered light regardless the polarization direction). Consequently, the difference of a sensor signal equipped with a parallel polarizer and a sensor signal with an orthogonal polarizer contains hardly any scattered reflection, but only specular reflection which is non-pulsatile. This difference channel has a very low pulsatility, regardless the selected wavelength or SpO2 level, and would consequently provide a means to keep the angle of the PBV vector with the vector [1 1] large under all circumstances by providing a channel with always low pulsatility.

Figure 4:
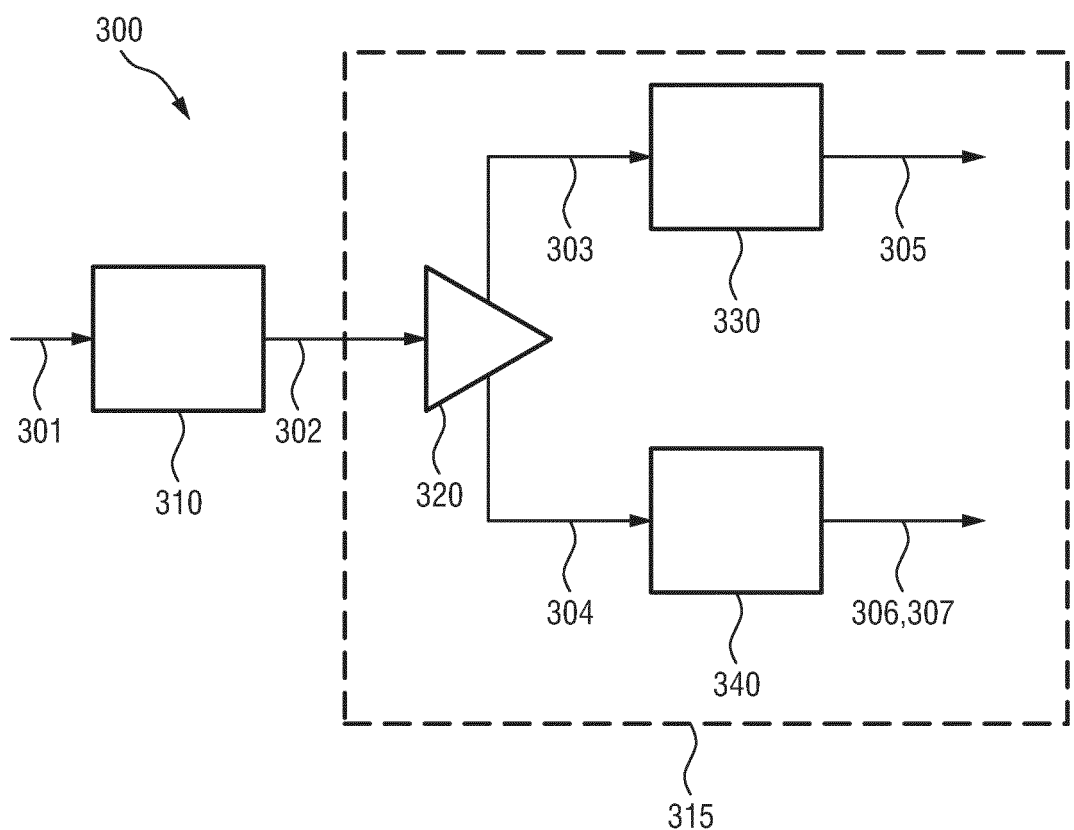
FIG. 4 shows a schematic diagram of a first embodiment of a device for obtaining detection signals including a first embodiment of a pre-treatment unit according to the present invention.

FIG. 4 shows a schematic diagram of a first embodiment of a device 300 for obtaining detection signals including a first embodiment of a pre-treatment unit 315 according to the present invention. Polarized illumination (polarized light) is emitted (by the illumination unit 140; see FIG. 2) to the skin of the subject. Light 301 reflected from the skin is received by the receiving element 310, e.g. an optical lens. The received light 302 is guided to an optical element 320, e.g. a polarization unit, that separates the cross and parallel polarized beams 303, 304 and projects them on separate sensors 330, 340 (together e.g. forming a sensor unit). In an exemplary embodiment the sensors 330, 340 are both equipped with a pixelated (Bayer) filter to acquire the different wavelength channel in parallel for each polarization direction. However, various alternatives exist.

In this embodiment, the polarization unit 320 (e.g. a prism or polarization filter) is generally configured to apply a first polarization on the received electromagnetic radiation 302 to generate first polarized radiation 303 and to apply a second polarization, which is different from the first polarization, or no polarization on the received electromagnetic radiation 302 to generate second polarized or non-polarized radiation 304. Further, the sensor unit comprising the sensors 330, 340 is generally configured to derive at least one detection signal 305 from the first polarized radiation 303 in a first wavelength channel and to derive at least two detection signals 306, 307 from the second polarized or non-polarized radiation 304 in the first wavelength channel and in a second wavelength channel.

In further embodiments it is provided that each sensor 330, 340 derives two or three detection signals in two or three wavelength channels, and or that the light beams 303, 304 are split further, separate wavelength selective filters are used in each path to a separate sensor.

Figure 5:
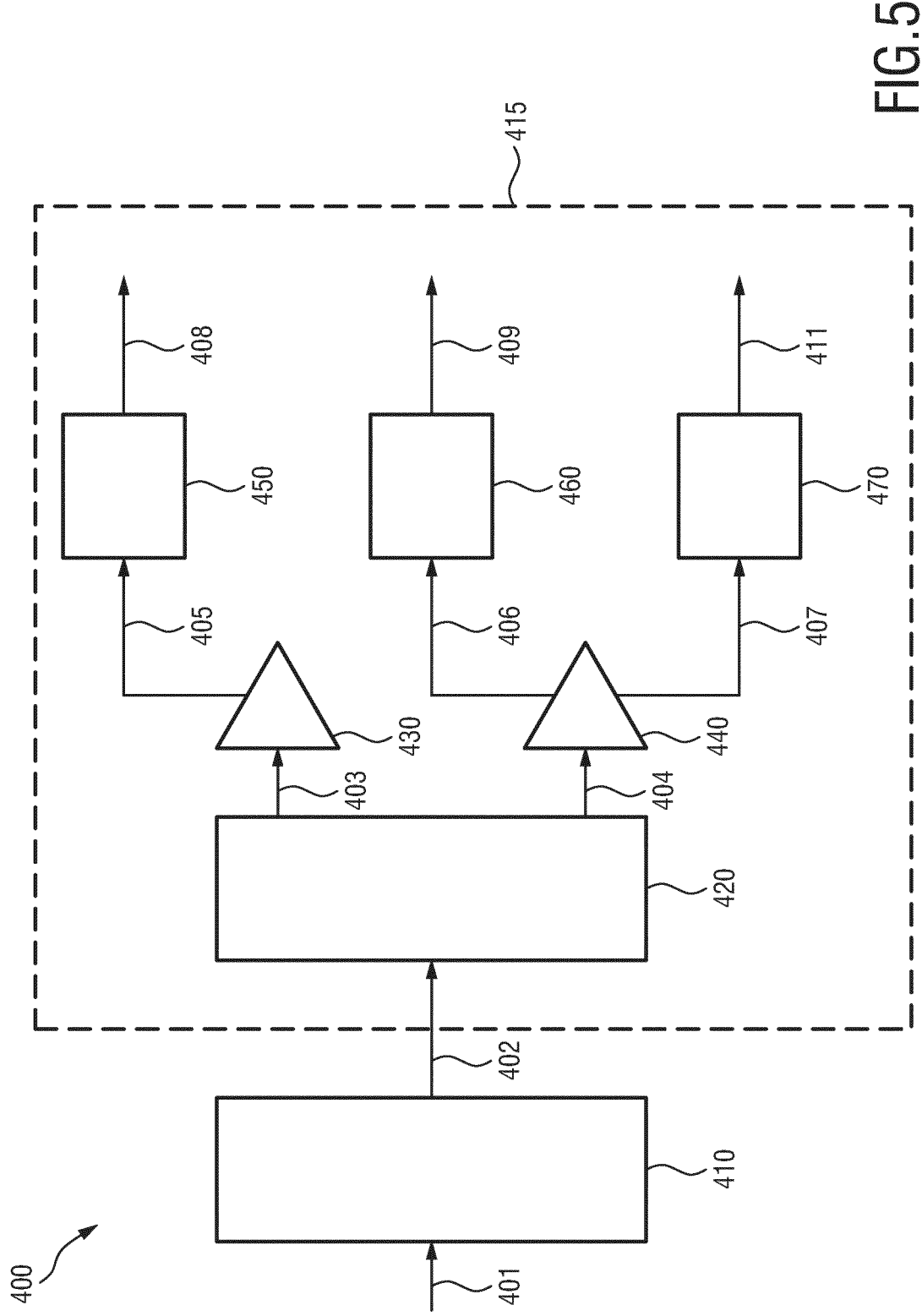
FIG. 5 shows a schematic diagram of a second embodiment of a device for obtaining detection signals including a second embodiment of a pre-treatment unit according to the present invention.

FIG. 5 shows a schematic diagram of a second embodiment of a device 400 for obtaining detection signals including a second embodiment of a pre-treatment unit 415 according to the present invention. In this embodiment the received light beam 401 is first split into different wavelength channels, while only one or more wavelength channels are equipped with at least one polarizer. In particular, in the embodiment shown in FIG. 5 there is generally provided a filter unit 420 (e.g. a prism or optical filter) that is configured to filter the electromagnetic radiation 402 that is received by the receiver 410 to generate first filtered radiation 403 in a first wavelength channel and second filtered radiation 404 in a second wavelength channel. A polarization unit, comprising e.g. two separate polarizers 430, 440, is configured to apply a first polarization on the first filtered radiation 403 to generate first polarized radiation 405 and to apply a second polarization, which is different from the first polarization, or no polarization on the first filtered radiation 403 and on the second filtered radiation 404 to generate second polarized or non-polarized radiation 406 and third polarized or non-polarized radiation 407. A sensor unit, e.g. comprising two or three sensor elements 450, 460, 470, derives at least one detection signal 408, 409, 411 from each of the first polarized radiation 405 and the second and third polarized or non-polarized radiation 406, 407.

Generally, as polarizer a polarization filter may be used. However, for this purpose, not only transmission filters can be employed, but reflectors and/or mirrors (e.g. polarization mirrors) may be used to achieve the same effect.

With each embodiment a single channel shall be provided that has low pulsatility to obtain a PBV vector with a favorable angle with vector [1 1 1]. On the other hand, one or more of the other channels may profit from using cross polarizers, as this increases the pulsatility in these channels by suppressing the specular reflection. This also improves the accuracy of the SpO2 measurement. In practice, price considerations may indicate, however, to not use this further improvement, as the specular reflection in the NIR spectrum can generally be kept reasonably small given the optical properties of the skin.

As explained above, the ABPV method needs at least two wavelengths, although using three wavelengths has been shown to improve the motion robustness. While for proper SpO2 measurement the relative pulsatility in two channels is required, it is preferred to obtain good motion robustness from a channel that uses parallel polarization but has little PPG modulation. An embodiment of the disclosed system and device may therefore e.g. use wavelengths of 760 nm (or 660 nm) and 810 nm (or 900 nm), where at least one of these wavelengths is also made available through a parallel polarizer, leading to three channels, e.g. the channels 760n, 810n and 810p, with index "n" indicating "no polarizer" and "p" indicating the use of a parallel polarizer and the number indicates the wavelength. In this case, the 810p channel has a reduced pulsatility, though the pulsatility may still be significant as the specular reflection may not be very large in the NIR part of the spectrum. Therefore, this is not a preferred embodiment for SpO2 measurement, but it could work well for heart rate extraction in the visible part of the spectrum, particularly if the parallel polarizer is used in the blue channel where specular reflection from the skin is much larger.

Another embodiment may use 760 nm (or 660 nm) and 810 nm (or 900 nm), where at least one of these wavelengths is made available through a parallel polarizer and through a cross-polarizer, building the following three channels, e.g.: 760c, (760p-760c), and 810c, with index "n" indicating "no polarizer", "p" indicating the use of a parallel polarizer, and index "c" indicating the use of a cross polarizer. In this case the SpO2 value becomes known from the first and the last channels (760c and 810c), while the second channel is a difference channel (of the difference between the 760p channel and the 760c channel), which has an almost completely suppressed pulsatility improving the motion robustness of the concept. This should work also when the first and last channels use no polarizer.

To further improve motion robustness, and/or to measure more blood species, and/or to define a reliability metric, three wavelengths (and three channels) may be used, e.g.: 760c, (810p-810c), 905c. In this case, again only one channel is made available with a parallel polarizer to improve the angle the PBV vector makes with [1 1 1]. This again is a choice, and more channels with parallel polarization can be included.

In advantageous embodiments, the wavelength dependent reflection information may concern wavelengths in the NIR range (700 nm to 1000 nm), where each of the channels may have a bandwidth between 10 nm and 100 nm. Particularly the shorter wavelengths may have a narrower bandwidth than the longer wavelengths to correct for decreasing sensitivity of the sensor, which often comprises Si as main element.

Further embodiments may be provided, e.g. an elaborated system enabling all options discussed in the above, i.e. which is able to provide e.g. six channels including three wavelength channel per polarization channel of two polarization channels (for parallel polarization and cross polarization).

Through the present invention an adaptation of the PBV or ABPV is presented such that the signature vector (PBV vector indicating the relative pulsatilities of different wavelength channels) includes a channel that always has a low pulsatility, even when the SpO2 value is low. This channel mainly contains the motion-induced distortions. Adding this always low-pulsatile channel to the PBV pulse extraction or the ABPV SpO2 measurement algorithm, or replacing an existing channel solves the reduced motion robustness problem of the known systems and methods.

The above described methods can be applied on detection signals that have been acquired using contactless sensors. By way of example, the present invention can be applied in the field of healthcare, e.g. unobtrusive remote patient monitoring, general surveillances, security monitoring and so-called lifestyle environments, such as fitness equipment or the like. Applications may include monitoring of oxygen saturation (pulse oximetry), pulse rate, blood pressure, cardiac output, changes of blood perfusion, assessment of autonomic functions, respiration and detection of peripheral vascular diseases. The present invention can e.g. be used for rapid and reliable pulse detection of a critical patient, for instance during automated CPR (cardiopulmonary resuscitation). The system can be used for monitoring of vital signs of neonates with very sensitive skin e.g. in NICUs and for patients with damaged (e.g. burnt) skin, but may also be more convenient than contact sensors as used in the general ward, and offer better solutions for motion robustness.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for extracting physiological information indicative of at least one vital sign of a subject, said device comprising:
   a pre-treatment unit capable of deriving at least three detection signals from electromagnetic radiation configured to be reflected from a skin region of the subject, wherein at least two detection signals comprise wavelength-dependent reflection information in a different wavelength channel and at least two detection signals comprise reflection information in different polarization channels having different polarization directions, wherein the pre-treatment unit is further capable of deriving two of the at least three detection signals comprising wavelength-dependent reflection information in the same wavelength channel but in different polarization channels and/or to derive one of the at least three detection signals as a difference detection signal representing the difference between first reflection information in a first wavelength channel and a first polarization channel having a first polarization direction and second reflection information in the first wavelength channel and a second polarization channel having a second polarization direction different from the first polarization direction;
   a pulse signal computation unit capable of computing at least two pulse signals from said at least three detection signals using different given signature vectors, wherein for the computation of each pulse signal a different given signature vector is used, wherein a given signature vector represents expected relative pulsatilities of the respective pulse signal in the at least three detection signals, wherein the computation of a pulse signal involves computing a weighted combination of the at least three detection signals using weights resulting in a pulse signal for which the products with the original detection signals equals the relative pulsatilities as represented by the respective signature vector;
   a quality indicator computation unit capable of computing quality indicator values for said pulse signals indicating a characteristic of the respective pulse signal; and
   a processor capable of deriving physiological information indicative of at least one vital sign from the signature vector that results in the pulse signal with the best quality indicator value and/or from said pulse signal with the best quality indicator value itself.

2. The device as claimed in claim 1, wherein said pre-treatment unit comprises:
   a polarizer capable of applying a first polarization on the received electromagnetic radiation to generate a first polarized radiation and applying a second polarization, which is different from the first polarization, or no polarization on the received electromagnetic radiation to generate a second polarized or non-polarized radiation; and
   a sensor capable of deriving at least one detection signal from the first polarized radiation in a first wavelength channel and to derive at least two detection signals from the second polarized or non-polarized radiation in the first wavelength channel and in a second wavelength channel.

3. The device as claimed in claim 1, wherein said pre-treatment unit comprises:
   a filter capable of filtering the received electromagnetic radiation to generate a first filtered radiation in a first wavelength channel and a second filtered radiation in a second wavelength channel;
   a polarizer capable of applying a first polarization on the first filtered radiation to generate a first polarized radiation and capable of applying a second polarization, which is different from the first polarization, or no polarization on the first filtered radiation and on the second filtered radiation to generate a second polarized or non-polarized radiation and a third polarized or non-polarized radiation; and
   a sensor capable of deriving at least one detection signal from each of the first polarized radiation and the second and the third polarized or non-polarized radiation.

4. The device as claimed in claim 1, wherein said pre-treatment unit is capable of deriving at least two detection signals comprising reflection information in two different polarization channels having orthogonal polarization directions.

5. The device as claimed in claim 4, wherein said pre-treatment unit is capable of deriving:
   a first detection signal comprising reflection information in a first polarization channel having a first polarization direction, which is parallel to the polarization direction of polarized electromagnetic radiation configured to illuminate the skin region of the subject; and
   a second detection signal comprising reflection information in a second polarization channel having a second polarization direction, which is orthogonal to the polarization direction of polarized electromagnetic radiation configured to illuminate the skin region of the subject.

6. The device as claimed in claim 1, wherein said pre-treatment unit is capable of deriving:
   a first detection signal comprising reflection information in a first wavelength channel and a first polarization channel having a first polarization direction, which is parallel to the polarization direction of polarized electromagnetic radiation configured to illuminate the skin region of the subject;
a second detection signal comprising reflection information in the first wavelength channel and a second non-polarized polarization channel; and
a third detection signal comprising reflection information in a second wavelength channel, different from the first wavelength channel, and the second non-polarized polarization channel.

7. The device as claimed in claim 1, wherein said pre-treatment unit is capable of deriving:
a first detection signal comprising reflection information in a first wavelength channel and a first polarization channel having a first polarization direction, which is parallel to the polarization direction of polarized electromagnetic radiation configured to illuminate the skin region of the subject;
a second detection signal comprising reflection information in the first wavelength channel and a second polarization channel having a second polarization direction, which is orthogonal to the polarization direction of polarized electromagnetic radiation configured to illuminate the skin region of the subject; and
a third detection signal comprising reflection information in a second wavelength channel, different from the first wavelength channel, and the second polarization channel.

8. The device as claimed in claim 7, wherein said pre-treatment unit is capable of deriving a fourth detection signal comprising reflection information in a third wavelength channel, different from the first and the second wavelength channels, and the second polarization channel.

9. The device as claimed in claim 1,
wherein said pre-treatment unit and/or said pulse signal computation unit is capable of deriving a difference detection signal representing the difference between a first reflection information in a first wavelength channel and a first polarization channel having a first polarization direction and a second reflection information in the first wavelength channel and a second polarization channel having a second polarization direction different from the first polarization direction; and
wherein said pulse signal computation unit is capable of using said difference detection signal as one of the detection signals for computing the at least two pulse signals.

10. The device as claimed in claim 1, wherein said pulse signal computation unit is capable of computing the at least two pulse signals $S_1$, $S_2$ by computing a covariance matrix $Q=C_n C_n^T$ of normalized DC-free detection signals $C_n$ over a time window and find the weights $W_x$ to compute a pulse signal $S_x=\vec{W}_x C_n$ as $\vec{W}_x=k\vec{P}_{bvx}Q^{-1}$, where k is chosen to make $\|\vec{W}_x\|=1$ and $x \in \{1, 2\}$.

11. The device as claimed in claim 1, wherein said pulse signal computation unit is capable of using a fixed or an adaptive set of different signature vectors and said processor is capable of filtering a time sequence of the signature vectors that resulted in the pulse signal with the best quality indicator value to obtain a filtered signature vector from which the physiological information is derived, wherein said time sequence of signature vectors is obtained from the pulse signals and the quality indicators computed for successive time windows of said at least two detection signals.

12. A system for extracting physiological information indicative of at least one vital sign of a subject, said system comprising:
a receiver capable of receiving electromagnetic radiation configured to be reflected from a skin region of the subject; and
the device of claim 1.

13. The system as claimed in claim 12,
further comprising an illuminator configured to illuminate the skin region of the subject with linearly polarized electromagnetic radiation, in particular within a wavelength range from 300 nm to 1000 nm.

14. A method for extracting physiological information indicative of at least one vital sign of a subject, said method comprising:
deriving at least three detection signals (CO from electromagnetic radiation configured to be reflected from a skin region of a subject, wherein at least two detection signals comprise wavelength-dependent reflection information in a different wavelength channel and at least two detection signals comprise reflection information in different polarization channels having different polarization directions, wherein two of the at least three detection signals are derived comprising wavelength-dependent reflection information in the same wavelength channel but in different polarization channels and/or one of the at least three detection signals is derived as a difference detection signal representing the difference between first reflection information in a first wavelength channel and a first polarization channel having a first polarization direction and second reflection information in the first wavelength channel and a second polarization channel having a second polarization direction different from the first polarization direction;
computing at least two pulse signals from said at least three detection signals using different given signature vectors, wherein for the computation of each pulse signal a different given signature vector is used, wherein the given signature vector represents expected relative pulsatilities of the respective pulse signal in the at least three detection signals, wherein the computation of a pulse signal involves computing a weighted combination of the at least three detection signals using weights resulting in a pulse signal for which the products with the original detection signals equals the relative pulsatilities as represented by the respective signature vector;
computing quality indicator values for said pulse signals indicating a characteristic of the respective pulse signal; and
deriving the physiological information indicative of the at least one vital sign from the signature vector that results in the pulse signal with the best quality indicator value and/or from said pulse signal with the best quality indicator value itself.

15. A device for obtaining detection signals allowing to extract physiological information indicative of at least one vital sign of a subject, said device comprising:
a receiver capable of receiving electromagnetic radiation configured to be reflected from a skin region of a subject; and
a pre-treatment unit capable of deriving at least three detection signals ($C_n$) from electromagnetic radiation reflected from a skin region of a subject, wherein at least two detection signals comprise wavelength-dependent reflection information in a different wavelength channel and at least two detection signals comprise reflection information in different polarization channels having different polarization directions;

wherein the pre-treatment unit is further capable of deriving one of the at least three detection signals as a difference detection signal representing the difference between a first reflection information in a first wavelength channel and a first polarization channel having a first polarization direction and a second reflection information in the first wavelength channel and a second polarization channel having a second polarization direction different from the first polarization direction.

* * * * *